United States Patent
Gwak et al.

(10) Patent No.: US 8,927,774 B2
(45) Date of Patent: Jan. 6, 2015

(54) METHOD FOR SEPARATING AND PURIFYING 1,4-DIAMINOBUTANE FROM FERMENTED SOLUTION

(75) Inventors: Won Sik Gwak, Masan-si (KR); Soon Won Hong, Seoul (KR); Soo An Shin, Seoul (KR); Han Won Lee, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 14/240,695

(22) PCT Filed: Aug. 24, 2012

(86) PCT No.: PCT/KR2012/006761
§ 371 (c)(1),
(2), (4) Date: Mar. 18, 2014

(87) PCT Pub. No.: WO2013/028030
PCT Pub. Date: Feb. 28, 2013

(65) Prior Publication Data
US 2014/0213824 A1  Jul. 31, 2014

(30) Foreign Application Priority Data
Aug. 24, 2011 (KR) .................. 10-2011-0084728

(51) Int. Cl.
*C07C 209/00* (2006.01)
*C07C 209/86* (2006.01)
*C12P 13/00* (2006.01)
*C07C 209/84* (2006.01)

(52) U.S. Cl.
CPC ............ *C07C 209/86* (2013.01); *C12P 13/001* (2013.01); *C07C 209/84* (2013.01)
USPC .......................................... 564/497; 435/128

(58) Field of Classification Search
CPC ............................. C07C 213/10; C12P 13/001
USPC .......................................... 564/497; 435/128
See application file for complete search history.

(56) References Cited

U.S. PATENT DOCUMENTS

2009/0011478 A1* 1/2009 Eppelmann et al. .......... 435/128

FOREIGN PATENT DOCUMENTS

| JP | 2010-0057396 A | 3/2010 |
| KR | 2000-0013855 A | 3/2000 |
| KR | 10-2009-0072584 A | 7/2009 |
| KR | 10-2009-0107920 A | 10/2009 |

* cited by examiner

*Primary Examiner* — Sudhakar Katakam
(74) *Attorney, Agent, or Firm* — Seed IP Law Group PLLC

(57) ABSTRACT

The present invention relates to a method for separating and purifying 1,4-diaminobutane at high purity and high yield from a fermented solution comprising 1,4-diaminobutane, through cell mass removal, desalination, concentration, impurities removal, and recovery. Also, provided is a method for separating and purifying 1,4-diaminobutane at high purity and high yield from a fermented solution 1,4-diaminobutane, through cell mass removal, desalination, low-temperature concentration, crystallization, filtration, high-temperature concentration and distillation.

19 Claims, 2 Drawing Sheets

METHOD FOR SEPARATING AND PURIFYING 1,4-DIAMINOBUTANE FROM FERMENTED SOLUTION

TECHNICAL FIELD

The present invention relates to a method for separating and purifying 1,4-diaminobutane at high purity and high yield from fermented solution.

BACKGROUND ART 1,4-Diaminobutane (also known as putrescine), abundantly found in dead organisms and semen, is used as a monomer of polyamide-4,6 in the chemical industry. To date, the commercialized process has been a chemical process. In the process, succinonitrile is produced by reaction of hydrogen cyanide and acrylonitrile, and dehydrogenated to yield 1,4-diaminobutane, followed by purification. However, this chemical process suffers from the disadvantages of treating a highly toxic raw material, requiring a high temperature and a high pressure for hydrogenation, and using a highly expensive catalyst.

Thus, as an alternative to the chemical process, a carbon source derived from recyclable biomass is required for use in the production of 1,4-diaminobutane.

Recently, fermentation using variant microorganisms has been developed to produce 1,4-diaminobutane (Korean Patent Publication No. 10-2009-0107920). However, studies on separation and purification of 1,4-diaminobutane from fermented solution at high purity and high yield remain insufficient.

Leading to the present invention, intensive and thorough research into separation and purification of 1,4-diaminobutane, conducted by the present inventors, resulted in the finding that 1,4-diaminobutane can be separated and purified at a high purity and high yield through a series of processes including desalination by addition of an alkaline material to a cell mass-removed, fermented solution, removal of impurities by crystallization, and repeated cycles of recovery and concentration.

DISCLOSURE

Technical Problem

The present invention is to provide a method for separating and purifying 1,4-diaminobutane at high purity and high yield from a fermented solution comprising 1,4-diaminobutane, through cell mass removal, desalination, concentration, impurity removal, and recovery processes.

Technical Solution

In order to achieve the object thereof, the present invention provides a method for separating and purifying 1,4-diaminobutane from a fermented solution comprising 1,4-diaminobutane, comprising removing cell mass from the fermented solution (step 1); adding an alkaline material to the cell mass-removed, fermented solution of step 1 to remove produced salts (step 2); concentrating the desalted, fermented solution of step 2 (step 3); removing impurities from the concentrated, fermented solution of step 3 (step 4); and recovering 1,4-diaminobutane from the impurity-removed, fermented solution (step 5).

Step 1 is a step in which a cell mass is removed from a fermented solution comprising 1,4-diaminobutane which is produced through a fermentation process. So long as it contains cells modified to produce 1,4-diaminobutane, any fermented solution may be used in the present invention, irrespective of the kinds of the microorganisms employed. Available microorganisms are those which belong to *Escherichia, Enterobacter, Erwinia, Klebsiella, Pantoea, Serratia,* and *Coryne* forms.

The fermented solution used in the present invention using, for example, a *Corynebacterium* variant, an *E. coli* variant, etc., can produce 1,4-diaminobutane.

A method used to remove the cell mass from the fermented solution may employ a centrifuge, a filter press, a diatomaceous earth filter, a rotary vacuum filter, a membrane separator, or agglomeration and flotation, etc., but is not limited thereto.

The removed cell mass may be dried for use as foodstuffs for animals or as manure. The solution from which the cell mass is removed is transferred to a pH-adjusting storage tank.

Step 2 is to dissociate the salt produced during the fermentation by addition of an alkaline material to the cell mass-removed, fermented solution of step 1, so that the desalination facilitates the purification of 1,4-diaminobutane.

When 1,4-diaminobutane is in a free form in a culture medium, the pH of the solution becomes 11.2 or higher. When the pH is high, the cells cannot produce 1,4-diaminobutane, and undergo lysis. To prevent this, a neutralizing agent is added to the solution during fermentation. Predominantly, the neutralizing agent is sulfuric acid. The reason why hydrochloric acid is not employed is the occurrence of a problem with causticity.

In addition, the medium contains ammonium sulfate $((NH_4)_2SO_4)$ as an N source for 1,4-diaminobutane. Since $2NH_4^+$ of ammonium sulfate is used as an N source, the remaining moiety $SO_4^{2-}$ is present in a free form, or some reacts with 1,4-diaminobutane under a neutral condition to form a 1,4-diaminobutane salt $((CH_2)_4(NH_3^+)_2\text{—}SO_4^{2-})$. According to the kinds of N source, 1,4-diaminobutane may be present with an anion, such as $Cl^-$, other than $SO_4^{2-}$.

As mentioned above, the neutralizing agent neutralizes the cell mass-removed, fermented solution in terms of pH, and makes 1,4-diaminobutane present as a salt bound with an anion such as $SO_4^{2-}$ under the neutral condition, so that the 1,4-diaminobutane in the salt form is difficult to purify.

In the present invention, step 2 is introduced in order to easily separate 1,4-diaminobutane by adding an alkaline material the solution to remove the salt bound to the 1,4-diaminobutane.

This may be represented as shown in the following Reaction Scheme.

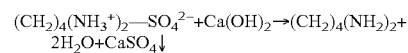

In order to remove the salt bound to 1,4-diaminobutane, an alkaline material is added to adjust the pH from 11.2 to 14.0. In the Reaction Scheme, $Ca(OH)_2$ serves as an alkaline material.

According to its chemistry, 1,4-diaminobutane takes a monovalent cation at a pH of 11.2 or less, and a divalent cation at a pH of 9.7 or less. Thus, at a low pH, 1,4-diaminobutane becomes a divalent cation, so that it associates with an anion (salt) and thus is difficult to purify. Hence, the solution must be preferably adjusted to a pH of 11.2 or higher, and more preferably to a pH of 11.2 to 14.0.

Examples of the alkaline material added in the present invention include sodium hydroxide, calcium hydroxide, magnesium hydroxide, potassium hydroxide, lithium hydroxide, and ammonium hydroxide.

The produced salt (calcium sulfate in the Reaction Scheme) may be segregated using a centrifuge, a filter press, a diatomaceous earth filter, a rotary vacuum filter, a membrane separator, or agglomeration and flotation, etc., but is not limited thereto.

The recovered salt (e.g., calcium sulfate) may be further purified for use as an additive or material in foods, cements, fertilizers, plaster casts, and medical gypsum. By this desalination according to the Reaction Scheme, mostly only the calcium sulfate is removed, because the other compounds, except for calcium sulfate, is not crystallized due to their high solubility in water.

Step 3 is designed to concentrate the fermented solution desalted in step 2, thus enhancing the purification yield of 1,4-diaminobutane.

Since after desalination, the remaining liquid is mostly water, the removal of water may take precedence over other steps. The concentrator may be selected from the group consisting of, but not limited to, a centrifugal concentrator, an evaporator, a natural circulation evaporator, a low-temperature vacuum evaporator, a rotary vacuum evaporator, a vacuum evaporator, a thin film evaporator, and a plate evaporator. Preferably, the fermented solution may be concentrated by a low-temperature method using a low-temperature vacuum evaporator. This low-temperature vacuum evaporator may be used under the condition set forth as follows:

A pressure condition is a pressure of 10 to 760 mmHg, and preferably 70 to 200 mmHg. A temperature condition is maintained at 10 to 100° C., and preferably at 45 to 67° C. In this regard, water is removed until the water content is reduced to 5 to 30 wt % and preferably to 10 to 25 wt %.

When the degree of concentration is high, the viscosity increases, making the filtration difficult. When the degree of concentration is low, impurities may not be formed as a precipitate, which makes the concentration meaningless in terms of purification. In addition, the purification yield may vary depending on the water % of the concentrate. If all water is removed, impurities become low in solubility and form fine precipitates which take a long time to filter. Along with the condensed liquid, the ammonia produced during fermentation is recovered. This by-product may be converted into ammonium sulfate using sulfuric acid.

Step 4 is a step in which impurities are removed from the fermented solution concentrated in step 3, contributing to an improvement in the purification yield of 1,4-diaminobutane.

Impurities present in the concentrated, fermented solution may be removed using various methods, including, but not limited to, a centrifuge, a filter press, a diatomaceous earth filter, a rotary vacuum filter, a membrane separator, agglomeration and flotation, or a filter paper. After filtration, the liquid is used in the step of recovering 1,4-diaminobutane while the solids are discarded.

Optionally, the method may further comprise a crystallization step between steps 3 and 4. By further comprising crystallizing the concentrated, fermented solution after the step of concentrating the desalted, fermented solution, impurities can be removed as crystal growth proceeds during the crystallization of the fermented solution. In addition, the purification yield can be further increased by the crystal growth through the crystallization of the fermented solution.

For the crystallization, a process including, but not limited to, cooling crystallization, salting-out crystallization, drowning-out crystallization, solution crystallization, melting crystallization and seed crystallization may be used. Preferable is a process excluding the use of an additional ingredient because the ingredient, if added, must be removed. Specifically cooling crystallization may be used. Briefly, cooling crystallization may be performed by cooling the fermented solution at a rate of 0.01° C./min~10° C./min, and preferably at a rate of 0.05° C./min~1.0° C./min to 20° C.

Step 5 is a step in which 1,4-diaminobutane is recovered from the impurity-deprived, fermented solution of step 4. 1,4-diaminobutane can be separated from the impurity-deprived, fermented solution.

For this recovery, high-temperature concentration and fractional distillation may be carried out in succession. In detail, steam from the high-temperature concentration process is allowed to enter a distillation column through an inlet positioned at a middle height of the distillation column.

The pressure conditions for the high-temperature concentration and the fractional distillation are under a pressure of 10 to 760 mmHg, and preferably under a pressure of 70 to 200 mmHg. The temperature conditions are a temperature of 30 to 158° C., and preferably a temperature of 80 to 120° C. In a specific embodiment of the present invention, distillation under the above pressure and temperature conditions allowed separation into water and ammonium in the upper part of the column, and 1,4-diaminobutane in the lower part of the column.

The lower-column liquid of high-temperature concentration is concentrated until the initial amount of the fermented solution is reduced to 2~10 wt %, and preferably to 4~8 wt %. The remainder in the high-temperature concentration may be cycled back to a low-temperature concentration process, so as to enhance the purification yield by the recycling and repeating the processes of the present invention. The present invention is repeated as these processes are cycled, thereby increasing the purification yield. In the present invention, the solution left after the high-temperature concentration is recycled back to the concentration of step 3.

In accordance with another aspect thereof, the present invention provides a method for separating and purifying 1,4-diaminobutane from a fermented solution comprising 1,4-diaminobutane, comprising removing cell mass from the fermented solution (step 1); adding an alkaline material to the cell mass-removed, fermented solution of step 1 to remove produced salts (step 2); concentrating the desalted, fermented solution of step 2 (step 3); crystallizing the fermented solution of step 3 (step 4); removing impurities from the crystallized, fermented solution of step 4 (step 5); and recovering 1,4-diaminobutane from the impurity-removed, fermented solution of step 5 (step 6).

Steps 1 to 3 are the same as are described for aforementioned steps 1 to 3. In addition, steps 5 and 6 are respectively correspondent to the aforementioned steps 4 and 5.

Step 4 is to crystallize the concentrated, fermented solution in which impurities are removed through crystal growth. Thus, this step further enhances the purification yield.

For crystal growth, the crystallization may be accomplished using a process including, but not limited to, cooling crystallization, salting-out crystallization, drowning-out crystallization, solution crystallization, melting crystallization and seed crystallization. Preferable is a process excluding the use of an additional ingredient because the ingredient, if added, must be removed. Specifically cooling crystallization may be used. Briefly, cooling crystallization may be performed by cooling the fermented solution at a rate of 0.01° C./min~10° C./min, and preferably at a rate of 0.05° C./min~1.0° C./min to 20° C.

Advantageous Effects

According to the method for separating and purifying 1,4-diaminobutane from a fermented solution comprising 1,4- diaminobutane, the cell mass removed from the fermented solution may be used as foodstuffs for animals while the salts removed from the fermented solution are applicable for industrial additives. In addition, 1,4-diaminobutane can be produced at high purity and high yield through the concentration and distillation of the remaining solution.

MODE FOR INVENTION

Figure 1:
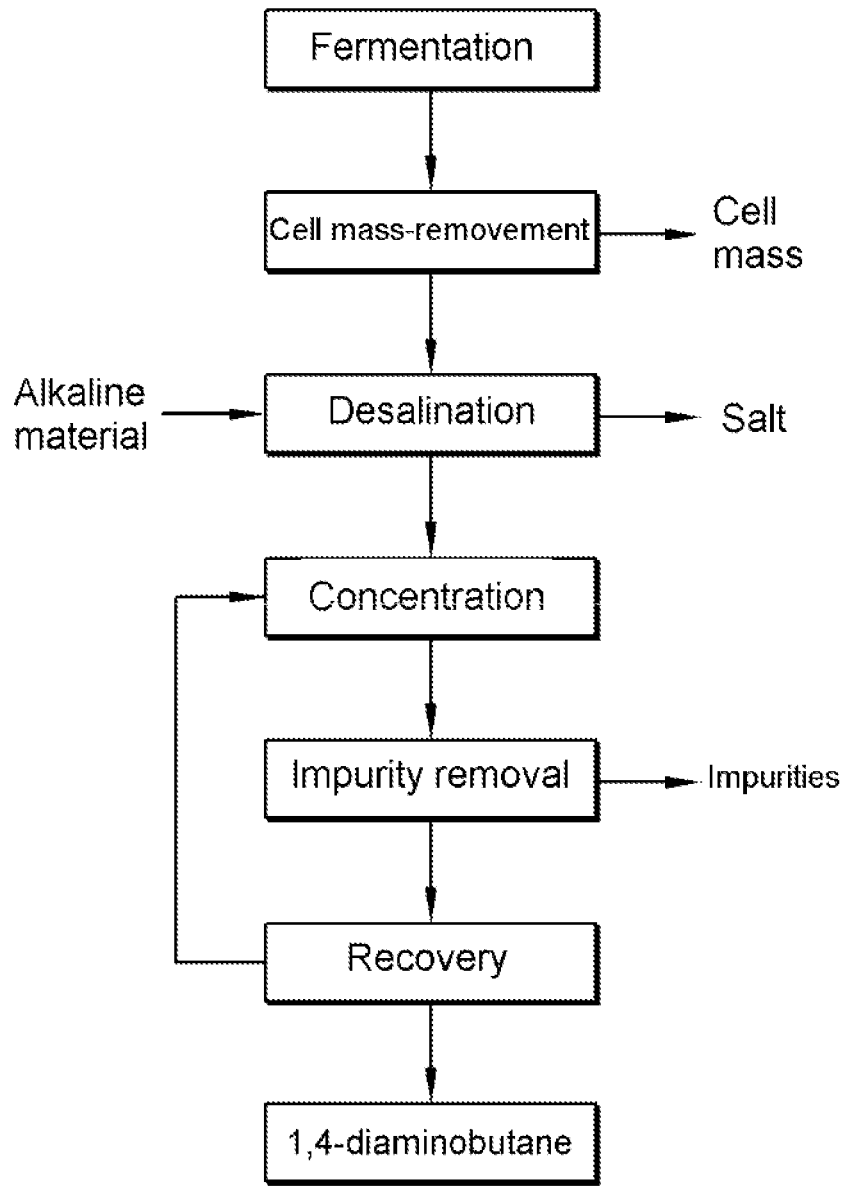
FIG. 1 is a flow chart illustrating a method for separating and purifying 1,4-diaminobutane at high purity and high yield from a solution containing 1,4-diaminobutane produced as a result of fermentation, through cell mass removement, desalination, concentration, impurities removal, and recovery.
Figure 2:
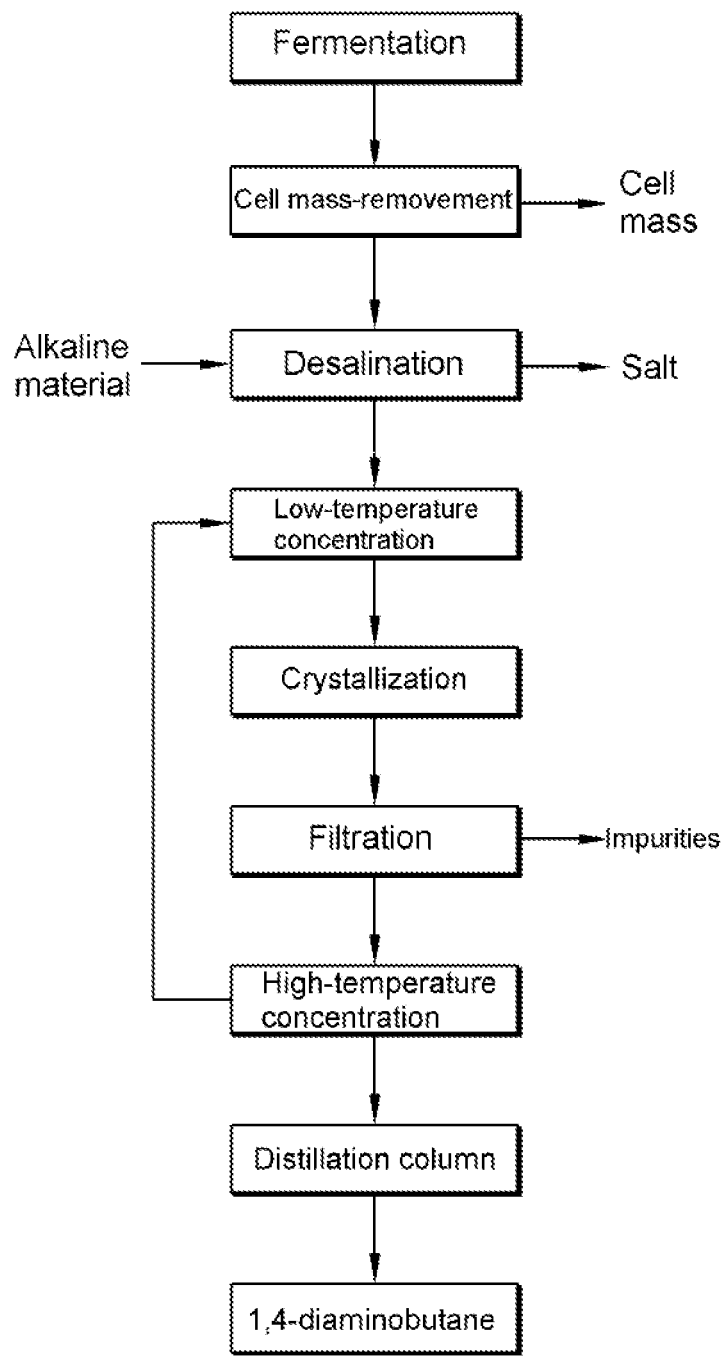
FIG. 2 is a flow chart illustrating a method for separating and purifying 1,4-diaminobutane at high purity and high yield from a solution containing 1,4-diaminobutane produced as a result of fermentation, through cell mass removement, desalination, low-temperature concentration, crystallization, filtration, high-temperature concentration, and distillation.

A better understanding of the present invention may be obtained through the following examples which are set forth to illustrate, but are not to be construed as limiting the present invention.

Crude 1,4-diaminobutane, amino acids, organic acids, and ions were analyzed using high pressure liquid chromatography (hereinafter referred to as "HPLC") while purified 1,4-diaminobutane was measured using gas chromatography (hereinafter referred to as "GC"). For water determination, a Kaal-Fischer titration method was used.

Example 1

Preparation of Fermented Solution Comprising 1,4-Diaminobutane, and Cell Mass-Removal from the Solution A fermented solution comprising 1,4-diaminobutane was prepared according to the description of Korean Patent Application No. 10-2010-124867. In detail, a *Korynebacterium* microorganism capable of producing putrescine which was modified to downregulate the expression of an ornithine carbamoyl transferase-encoding gene (argF) and a glutamate exporter-encoding gene (Ncgl1221) or to decrease the activity of the said gene expression products, and to have an ornithine decarboxylase-encoding gene (speC) introduced thereinto was cultured.

Then, 5,050 g of the fermented solution was placed in a 10 L beaker, and the cell mass was removed using a membrane separator. The membrane separator was in a cassette form, identified as Pellicon 2 of Millipore, with a pore size of 0.1 μm and an area of 0.5 $m^2$. The membrane filter body, a product of Millipore, consists of a cell feeding inlet, a circulation path, and a cell mass-removed liquid outlet. After filtration, 255.1 g of the solution containing the cell mass was removed, then 4794.9 g of the cell-free effluent was out. The compositions are summarized in Table 1, below.

TABLE 1

| Ingredient | Before removal of cell mass | solution containing cell mass | cell-free solutiont |
|---|---|---|---|
| Water | 3752.6 g | 3565.0 g | 187.6 g |
| Cell mass | 50.0 g | 0.0 g | 50.0 g |
| 1,4-Diaminobutane | 500.0 g | 490.0 g | 10.0 g |
| Amino acids | 44.5 g | 44.0 g | 0.5 g |
| Ions | 695.8 g | 688.9 g | 6.9 g |
| Organic acids | 7.1 g | 7.0 g | 0.1 g |
| Sum | 5050.0 g | 4794.9 g | 255.1 g |

Example 2

Desalination

In a 10 L beaker, 4794.9 g of the cell-free solution of Example 1 was stirred at room temperature, fed with 528.9 g of calcium hydroxide at a rate of 17.6 g/min. Following 2 hrs of stirring, the salt thus formed was removed by centrifugation. The salt was calcium sulfate, and amounted to 1123.3 g containing water.

Example 3

Low-Temperature Concentration

In a 5 L concentrator of Eyela, 4200.5 g of the solution of Example 2 was concentrated under a pressure of 80 mmHg at a steam temperature of 47° C. by 70%, 75%, and 80%. For the 70% concentration, the condensed liquid removed amounted to 2899.9 g inclusive of 1.0 g of 1,4-diaminobutane.

Compositions of the solution in each step were analyzed by % concentration, and the results are given in Tables 2 and 3. Yield was 39.2% upon 70% concentration and 45.8% upon 75% concentration. For 80% concentration, the yield was 11.3% and 17.9% higher than those of 75% and 70% concentrations, respectively.

TABLE 2

| | 70% $H_2O$ Concentration in Low-Temperature Concentrator | | | | | | |
|---|---|---|---|---|---|---|---|
| Ingredient | Solution fed to low-temp. concentrator | Condensed liquid from low-temp. concentrator | Filtrate/ Crystal after low-temp. condensation | Filtrate/ solution after low-temp. condensation | High-temp. concentrate | Liquid in upper distillation column | Liquid in lower distillation column |
| Water | 3624.9 g | 2537.1 g | 3.8 g | 1084.0 g | 0.0 g | 1083.8 g | 0.2 g |
| 1,4-Diaminobutane | 480.2 g | 0.4 g | 1.7 g | 478.2 g | 282.1 g | 0.0 g | 196.0 g |
| Amino acids | 43.2 g | 0.0 g | 11.7 g | 31.5 g | 31.5 g | 0.0 g | 0.0 g |

TABLE 2-continued

70% H₂O Concentration in Low-Temperature Concentrator

| Ingredient | Solution fed to low-temp. concentrator | Condensed liquid from low-temp. concentrator | Filtrate/Crystal after low-temp. condensation | Filtrate/solution after low-temp. condensation | High-temp. concentrate | Liquid in upper distillation column | Liquid in lower distillation column |
|---|---|---|---|---|---|---|---|
| Ions | 45.4 g | 0.0 g | 22.0 g | 23.5 g | 11.7 g | 11.8 g | 0.0 g |
| Organic acids | 6.8 g | 0.0 g | 2.5 g | 4.3 g | 4.3 g | 0.0 g | 0.0 g |
| Sum | 4200.5 g | 2537.4 g | 41.6 g | 1621.5 g | 329.6 g | 1095.6 g | 196.2 g |
| Yield | | | | Finally 39.2% recovered | | | |

TABLE 3

75% H₂O Concentration in Low-Temperature Concentrator

| Ingredient | Solution fed to low-temp. concentrator | Condensed liquid from low-temp. concentrator | Filtrate/Crystal after low-temp. condensation | Filtrate/solution after low-temp. condensation | High-temp. concentrate | Liquid in upper distillation column | Liquid in lower distillation column |
|---|---|---|---|---|---|---|---|
| Water | 3624.9 g | 2718.1 g | 5.9 g | 900.9 g | 0.0 g | 900.7 g | 0.2 g |
| 1,4-Diaminobutane | 480.2 g | 0.6 g | 2.4 g | 477.2 g | 248.1 g | 0.0 g | 229.1 g |
| Amino acids | 43.2 g | 0.0 g | 15.8 g | 27.3 g | 27.3 g | 0.0 g | 0.0 g |
| Ions | 45.4 g | 0.0 g | 24.4 g | 21.0 g | 9.6 g | 11.4 g | 0.0 g |
| Organic acids | 6.8 g | 0.0 g | 2.9 g | 4.0 g | 4.0 g | 0.0 g | 0.0 g |
| Sum | 4200.5 g | 2718.7 g | 51.5 g | 1430.4 g | 289.0 g | 912.1 g | 229.3 g |
| Yield | | | | Finally 45.8% recovered | | | |

Example 4

Impurities Removal 4-1) In Case that Only High-Temperature Filtration was Carried Out After the concentration of Example 3, the remaining fermented solution, amounting to 1300.6 g, was filtered using a double-jacket crystallizer at a high temperature to remove impurities.

4-2) In Case that Crystallization and Filtration were Carried Out

After the concentration of Example 3, the remaining fermented solution, amounting to 1300.6 g, was transported to a 2 L double-jacket crystallizer wherein the temperature was decreased from 50° C. to 20° C. at a cooling rate of 0.01° C./min. At 20° C., the solution was maintained for 1 hr, followed by filtration. The crystalline filtrate weighed 65.4 g inclusive of water.

Comparison of compositions between 4-1) and 4-2) is summarized in Table 4, below. As shown in the data, crystallization+filtration of section 4-2) removed impurities at higher efficiency than high-temperature filtration of section 4-1).

TABLE 4

| Ingredient | 4-1) High-Temp. Filtration | 4-2) Crystallization + Filtration |
|---|---|---|
| Water | 5.3 g | 8.5 g |
| 1,4-Diaminobutane | 1.4 g | 3.4 g |
| Amino acids | 8.6 g | 22.9 g |
| Ions | 23.4 g | 26.9 g |
| Organic acids | 1.6 g | 3.8 g |
| Sum | 40.4 g | 65.4 g |

Example 5

Recovery

To recover 1,4-diaminobutane from the concentrate of Example 4, high-temperature concentration and fractional distillation were carried out.

1235.2 g of the impurity-deprived solution was fed to a 2 L double-jacket reactor the top of which was connected to a middle point of a distillation column. This distillation column was a 30-stage column in a tray-type, commercially available from Ace Glass, with a junction to the reactor positioned at the 11th stage from the bottom. The reactor was set forth under a pressure of 80 mmHg at a steam temperature of 50~90° C. before experimentation. Its temperature was maintained at 47° C. during the initial water evaporation, and elevated to 90° C. with the concomitant vaporization of 1,4-diaminobutane. The vaporized gas was fed to the distillation column where water and ammonium were recovered in a total amount of 728.3 g to the upper column, with the recovery of 285.8 g of 1,4-diaminobutane (GC purity 99.9 wt %) in the lower column. The remainder amounting to 221.1 g in the double-jacket reactor was cycled to a condenser.

Compositions in recovery steps subsequent to the impurities removal of Example 4 are summarized in Table 5, below. The yield after the crystallization step was 18.9% higher than that after the high-temperature filtration alone.

TABLE 5

| Ingredient | 4-1) High-Temp. Filtration | | | | 4-2) Crystallization + Filtration | | | |
| --- | --- | --- | --- | --- | --- | --- | --- | --- |
| | Liquid for high-temp. concentration | High-temp. concentrate | Liquid in upper column | Liquid in lower column | Liquid for high-temp. concentration | High-temp. concentrate | Liquid in upper column | Liquid in lower column |
| Water | 720.7 g | 0.0 g | 720.5 g | 0.2 g | 717.4 g | 0.0 g | 717.1 g | 0.3 g |
| 1,4-Diaminobutane | 477.8 g | 286.7 g | 0.0 g | 191.1 g | 475.9 g | 190.4 g | 0.0 g | 285.5 g |
| Amino acid | 34.5 g | 34.5 g | 0.0 g | 0.0 g | 20.3 g | 20.3 g | 11.1 g | 0.0 g |
| Ions | 22.0 g | 10.2 g | 11.8 g | 0.0 g | 18.5 g | 7.4 g | 0.0 g | 0.0 g |
| Organic acid | 5.2 g | 5.2 g | 0.0 g | 0.0 g | 3.1 g | 3.1 g | 0.0 g | 0.0 g |
| Sum | 1260.2 g | 336.6 g | 732.2 g | 191.3 g | 1235.2 g | 221.1 g | 728.3 g | 285.8 g |
| Total Yield | | 38.2% | | | | 57.1% | | |

Example 6

Continuous Circulation Process

The solution left after the high-temperature concentration of Example 5 was cycled back to the low-temperature reactor. After 10 cycles, final compositions in each recovery step are given in Table 6. This recyclization resulted in a final yield of 94.6%.

TABLE 6

| Ingredient | Liquid fed to low-temp. reactor | Condensed liquid from low-temp. reactor | Filtrate/crystal after low-temp. concentration | Filtrate/solution after low-temp. concentration | Liquid for high-temp. concentration | Liquid in upper column | Liquid in lower column |
| --- | --- | --- | --- | --- | --- | --- | --- |
| Water | 3624.9 g | 2898.3 g | 13.1 g | 713.5 g | 0.0 g | 713.0 g | 0.5 g |
| 1,4-diaminobutane | 795.6 g | 1.6 g | 5.6 g | 788.4 g | 315.4 g | 0.0 g | 473.1 g |
| Amino acid | 81.5 g | 0.0 g | 43.2 g | 38.3 g | 38.3 g | 0.0 g | 0.0 g |
| Ion | 53.8 g | 0.0 g | 31.8 g | 22.0 g | 8.4 g | 13.6 g | 0.0 g |
| Organic acid | 12.4 g | 0.0 g | 6.8 g | 5.6 g | 5.6 g | 0.0 g | 0.0 g |
| Sum | 4568.2 g | 2899.9 g | 100.5 g | 1567.8 g | 367.7 g | 726.6 g | 473.5 g |
| Yield | | | | Final 94.6% | | | |

The invention claimed is:

1. A method for separating and purifying 1,4-diaminobutane from a fermented solution comprising 1,4-diaminobutane, comprising:
    removing cell mass from the fermented solution (step 1);
    adding an alkaline material to the cell mass-removed fermented solution of step 1 to remove produced salts (step 2);
    concentrating the desalted, fermented solution of step 2 (step 3);
    removing impurities from the concentrated, fermented solution of step 3 (step 4); and
    recovering 1,4-diaminobutane from the impurity-removed, fermented solution (step 5).

2. The method according to the claim 1, wherein the alkaline material is selected from the group consisting of sodium hydroxide, calcium hydroxide, magnesium hydroxide, potassium hydroxide, lithium hydroxide, and ammonium hydroxide.

3. The method according to the claim 1, wherein the concentrating of step 3 is carried out by low-temperature concentration.

4. The method according to the claim 3, wherein the low-temperature concentration is carried out by removing condensed liquid under a pressure of 10 mmHg to 760 mmHg at a steam temperature of 10° C. to 100° C.

5. The method according to the claim 1, wherein concentrating the fermented solution of step 3 is carried out until the concentrate has a water content of 5 to 30 wt %.

6. The method according to the claim 1, further comprising a crystallization step between step 3 and step 4.

7. The method according to the claim 1, wherein the recovering of step 5 is carried out by performing high-temperature concentration and fractional distillation in succession.

8. The method according to the claim 7, wherein the high-temperature concentration is carried out by concentrating the impurity-removed, fermented solution under a pressure of 10 to 760 mmHg at a temperature of 30 to 158° C. to form condensed liquid, and by feeding the condensed liquid to a distillation column.

9. The method according to the claim 8, wherein water and ammonium are recovered in an upper part of the distillation column while 1,4-diaminobutane is recovered in a lower part of the distillation column.

10. The method according to the claim 1, wherein the recovery of step 5 is carried out by cycling the fermented solution left after the high-temperature concentration back to the step 3.

11. A method for separating and purifying 1,4-diaminobutane from a fermented solution comprising 1,4-diaminobutane, comprising:
    removing cell mass from the fermented solution (step 1);
    adding an alkaline material to the cell mass-removed fermented solution of step 1 to remove produced salts (step 2);
    concentrating the desalted, fermented solution of step 2 (step 3);
    crystallizing the concentrated, fermented solution of step 3 (step 4);
    removing impurities from the crystallized, fermented solution of step 4 (step 5); and
    recovering 1,4-diaminobutane from the impurity-removed, fermented solution of step 5 (step 6).

12. The method according to the claim 11, wherein the alkaline material of step 2 is selected from the group consisting of sodium hydroxide, calcium hydroxide, magnesium hydroxide, potassium hydroxide, lithium hydroxide, and ammonium hydroxide.

13. The method according to the claim 11, wherein the concentrating of step 3 is carried out by low-temperature concentration.

14. The method according to the claim 13, wherein the low-temperature concentration is carried out by removing condensed liquid under a pressure of 10 mmHg to 760 mmHg at a steam temperature of 10° C. to 100° C.

15. The method according to the claim 11, wherein the crystallizing of step 4 is carried out by cooling the fermented solution at a cooling rate of 0.05° C./min to 1.0° C./min.

16. The method according to the claim 11, wherein the recovering of step 6 is carried out by performing high-temperature concentration and fractional distillation in succession.

17. The method according to the claim 16, wherein the high-temperature concentration is carried out by concentrating the impurity-removed fermented solution under a pressure of 10 to 760 mmHg at a temperature of 30 to 158° C. to form condensed liquid, and by feeding the condensed liquid to a distillation column.

18. The method according to the claim 17, wherein water and ammonium are recovered in an upper part of the distillation column while 1,4-diaminobutane is recovered in a lower part of the distillation column.

19. The method according to the claim 11, wherein the fermented solution left after the high-temperature concentration is cycled back to the step 3.

\* \* \* \* \*